(12) United States Patent
Sauer et al.

(10) Patent No.: US 10,460,204 B2
(45) Date of Patent: Oct. 29, 2019

(54) METHOD AND SYSTEM FOR IMPROVED HEMODYNAMIC COMPUTATION IN CORONARY ARTERIES

(71) Applicant: Siemens Healthcare GmbH, Erlangen (DE)

(72) Inventors: Frank Sauer, Princeton, NJ (US); Yefeng Zheng, Princeton Junction, NJ (US); Puneet Sharma, Monmouth Junction, NJ (US); Bogdan Georgescu, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/662,487

(22) Filed: Jul. 28, 2017

(65) Prior Publication Data

US 2017/0323177 A1 Nov. 9, 2017

Related U.S. Application Data

(63) Continuation of application No. 14/706,142, filed on May 7, 2015, now Pat. No. 9,747,525.

(Continued)

(51) Int. Cl.
*G06K 9/62* (2006.01)
*G06T 7/00* (2017.01)
(Continued)

(52) U.S. Cl.
CPC ............ *G06K 9/6218* (2013.01); *A61B 34/10* (2016.02); *A61B 90/37* (2016.02); *G06K 9/6256* (2013.01); *G06K 9/6277* (2013.01); *G06K 9/66* (2013.01); *G06T 7/0012* (2013.01); *G06T 7/11* (2017.01); *G06T 7/143* (2017.01);
(Continued)

(58) Field of Classification Search
None
See application file for complete search history.

(56) References Cited

U.S. PATENT DOCUMENTS

| | | | |
|---|---|---|---|
| 5,409,010 A | 4/1995 | Beach et al. | |
| 6,385,332 B1 * | 5/2002 | Zahalka | G06T 7/0012 128/922 |

(Continued)

FOREIGN PATENT DOCUMENTS

| | | |
|---|---|---|
| CN | 101523437 | 9/2009 |
| CN | 102411795 | 4/2012 |

OTHER PUBLICATIONS

Office Action dated Mar. 23, 2018 in corresponding Chinese Patent Application No. 201510589311.0.
(Continued)

*Primary Examiner* — Nancy Bitar

(57) ABSTRACT

Systems and methods for non-invasive assessment of an arterial stenosis, comprising include segmenting a plurality of mesh candidates for an anatomical model of an artery including a stenosis region of a patient from medical imaging data. A hemodynamic index for the stenosis region is computed in each of the plurality of mesh candidates. It is determined whether a variation among values of the hemodynamic index for the stenosis region in each of the plurality of mesh candidates is significant with respect to a threshold associated with a clinical decision regarding the stenosis region.

26 Claims, 6 Drawing Sheets

Related U.S. Application Data

(60) Provisional application No. 62/012,599, filed on Jun. 16, 2014.

(51) Int. Cl.
*A61B 90/00* (2016.01)
*G06K 9/66* (2006.01)
*A61B 34/10* (2016.01)
*G06T 7/11* (2017.01)
*G06T 7/143* (2017.01)

(52) U.S. Cl.
CPC ... *A61B 2034/105* (2016.02); *A61B 2034/107* (2016.02); *A61B 2034/108* (2016.02); *A61B 2090/374* (2016.02); *A61B 2090/378* (2016.02); *A61B 2090/3762* (2016.02); *A61B 2576/023* (2013.01); *G06K 2209/05* (2013.01); *G06T 2207/20124* (2013.01); *G06T 2207/30048* (2013.01); *G06T 2207/30101* (2013.01); *G06T 2207/30104* (2013.01)

(56) References Cited

U.S. PATENT DOCUMENTS

| | | | |
|---|---|---|---|
| 7,860,290 | B2 | 12/2010 | Gulsun et al. |
| 7,953,266 | B2 | 5/2011 | Gulsun et al. |
| 8,160,332 | B2 | 4/2012 | Von Berg et al. |
| 8,311,748 | B2 * | 11/2012 | Taylor ................ A61B 5/02007 702/19 |
| 9,082,048 | B2 | 7/2015 | Miller et al. |
| 9,595,089 | B2 | 3/2017 | Itu et al. |
| 10,278,662 | B2 * | 5/2019 | Ishii ................ A61B 6/463 |
| 2009/0012382 | A1 * | 1/2009 | Dutta ................ A61B 5/02007 600/407 |
| 2009/0088830 | A1 * | 4/2009 | Mohamed ............. A61F 2/91 623/1.11 |
| 2010/0067760 | A1 | 3/2010 | Zhang et al. |
| 2011/0131167 | A1 * | 6/2011 | Achterberg ............. G06F 17/11 706/46 |
| 2011/0224542 | A1 | 9/2011 | Mittal et al. |
| 2013/0064438 | A1 * | 3/2013 | Taylor ................ A61B 5/02007 382/130 |
| 2013/0226003 | A1 | 8/2013 | Edic et al. |
| 2014/0058715 | A1 | 2/2014 | Sharma et al. |
| 2014/0066765 | A1 | 3/2014 | Fan et al. |
| 2014/0107935 | A1 * | 4/2014 | Taylor ................ A61B 5/02007 702/19 |
| 2014/0114618 | A1 | 4/2014 | Fonte et al. |
| 2014/0180702 | A1 | 6/2014 | Mansker et al. |
| 2014/0200867 | A1 | 7/2014 | Lavi et al. |
| 2014/0270436 | A1 * | 9/2014 | Dascal ................ G06T 7/11 382/130 |
| 2014/0379269 | A1 | 12/2014 | Schmitt |
| 2015/0112182 | A1 | 4/2015 | Sharma et al. |
| 2015/0297161 | A1 * | 10/2015 | Grass ................ A61B 6/503 600/426 |
| 2015/0356734 | A1 * | 12/2015 | Ooga ................ A61B 6/03 382/131 |
| 2015/0359601 | A1 * | 12/2015 | Sauer ................ G06T 7/0012 382/128 |
| 2016/0296287 | A1 * | 10/2016 | Taylor ................ A61B 5/02007 |

OTHER PUBLICATIONS

Taylor, Charles A. et al. "Computational Fluid Dynamics Applied to Cardiac Computed Tomography for Noninvasive Quantification of Fractional Flow Reserve" Published by Elsevier Inc.;Journal of the American College of Cardiology, vol. 61, No. 22, 2013.

Wasilewski, Jaroslaw et al. "Invasive and non-invasive fractional flow reserve index in validation of hemodynamic severity of intracoronary lesions" New methods in diagnosis and therapy, 2013; pp. 160-169.

Cootes T.F. et al., "Active Shape Models—Their Training and Application", Computer Vision and Image Understanding, 61(1), Jan. 1995, pp. 38-59.

Lugauer F. et al.: "Improving Accuracy in Coronary Lumen Segmentation via Explicit Calcium Exclusion; Learning-based Ray Detection and Surface Optimization"; Progress in Biomedical Optics and Imaging Spie—International Society for Optical Engineering Bellingham US; vol. 9034; pp. 90343U-90343U; Mar. 21, 2014

De Bruyne et al., :Simultaneous Coronary Pressure and Flow Velocity Measurements in Humans. Feasibility, reproducibility, and hemodynamic dependence of coronary flow velocity reserve, hyperemic flow versus pressure slope index, and fractional flow reserve; 1996; 94:1842-1849,Oct. 15, 1996.

Zheng, et al., Four-Chamber Heart Modeling and Automatic Segmentation for 3D Cardiac CT Volumes Using Marginal Space Learning and Steerable Features,: IEEE Transactions on Medical Imaging, vol. 27, No. 11, Aug. 15, 2008, pp. 1668-1681.

Decision on Motions—BD. R. 121(a) entered Oct. 23, 2018 in Patent Interference No. 106,093 involving U.S. Pat. No. 9,747,525.

* cited by examiner

METHOD AND SYSTEM FOR IMPROVED HEMODYNAMIC COMPUTATION IN CORONARY ARTERIES

This application is a continuation of U.S. patent application Ser. No. 14/706,142, filed May 7, 2015, which claims the benefit of U.S. Provisional Application No. 62/012,599, filed Jun. 16, 2014, the disclosures of which are herein incorporated by reference in their entirety.

BACKGROUND OF THE INVENTION

The present invention relates generally to non-invasive computation of hemodynamic indices for an arterial stenosis, and more particularly to improving the accuracy of clinical decisions based on non-invasively computed hemodynamic indices.

Cardiovascular disease (CVD) is the leading cause of deaths worldwide. Among various CVDs, coronary artery disease (CAD) accounts for nearly fifty percent of those deaths. Despite significant improvements in medical imaging and other diagnostic modalities, the increase in premature morbidity and mortality for CAD patients is still very high. The current clinical practice for diagnosis and management of coronary stenosis involves the assessment of the diseased vessel either visually or by Quantitative Coronary Angiography (QCA). Such assessment provides the clinician with an anatomical overview of the stenosis segment and parent vessel, including the area reduction, lesion length, and minimal lumen diameter, but does not provide a functional assessment of the effect of the lesion on blood flow through the vessel. Measuring the fractional flow reserve (FFR) by inserting a pressure wire into the stenosed vessel has been shown to be a better option for guiding revascularization decisions, since the FFR is more effective in identifying ischemia causing lesions, as compared to invasive angiography. QCA only evaluates the morphological significance of the stenosis and has a number of other limitations. Pressure wire based FFR measurements involve risks associated with the intervention necessary to insert the pressure wire into the vessel, and for a very narrow stenosis, the pressure wire may induce an additional pressure drop.

BRIEF SUMMARY OF THE INVENTION

In accordance with an embodiment, systems and methods for non-invasive assessment of an arterial stenosis, comprising include segmenting a plurality of mesh candidates for an anatomical model of an artery including a stenosis region of a patient from medical imaging data. A hemodynamic index for the stenosis region is computed in each of the plurality of mesh candidates. It is determined whether a variation among values of the hemodynamic index for the stenosis region in each of the plurality of mesh candidates is significant with respect to a threshold associated with a clinical decision regarding the stenosis region.

In accordance with an embodiment, systems and methods for supporting a clinical decision regarding an anatomical object of interest include segmenting a plurality of mesh candidates for an anatomical model of an anatomical object of interest of a patient from medical imaging data. A quantitative metric is computed for each of the plurality of mesh candidates. It is determined whether a variation among values of the quantitative metric for each of the plurality of mesh candidates is significant regarding with respect to a threshold associated with a clinical decision regarding the anatomical object of interest.

These and other advantages of the invention will be apparent to those of ordinary skill in the art by reference to the following detailed description and the accompanying drawings.

DETAILED DESCRIPTION

The present invention generally relates to improving the workflow of a clinical decision based on hemodynamic indices. Embodiments of the present invention are described herein to give a visual understanding of methods for improving the workflow of a clinical decision. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Further, it should be understood that while the embodiments discussed herein may be discussed with respect to medical imaging data of a patient, the present principles are not so limited. Embodiments of the present invention may be employed for any imaging data.

Fractional flow reserve (FFR) is a functional measure for quantifying the hemodynamic significance of a stenosis in an artery. The FFR is typically determined based on the pressure drop over a coronary stenosis at hyperemia using invasive pressure wire based measurements. Hyperemia refers to a physiological state of the patient with more than normal blood flow. The clinical decision of whether or not to treat a coronary stenosis by placement of a stent may be based on the FFR value. For example, an FFR value of at least 0.8 may indicate that the stenosis is functionally not significant and treatment is not advised. However, an FFR value of less than 0.8 may indicate that the stenosis is functionally significant and treatment is advised.

The computational FFR (cFFR) seeks to replicate the FFR value via less invasive means. In one embodiment, the cFFR is determined by acquiring medical imaging data of a patient's heart with a computed tomography (CT) scanner, segmenting the medical imaging data to extract a geometrical model of the coronary arteries, and applying computational fluid dynamics to derive the FFR value of a coronary stenosis. The cFFR computation may result in a plurality of different FFR values due to variation in the segmentation results, which results in a plurality of geometrical model candidates. A conventional workflow involves a user selecting a best geometrical model candidate or editing segmentation results to determine the FFR value, which increases cost and requires additional time and effort from the user. However, in accordance with embodiments of the present invention, user input is not required if a range of results of the FFR value does not clinically impact a clinical decision. For example, if a range of results of the FFR value is above 0.8, the clinical decision to not treat the stenosis is not impacted and no user input or interaction is required.

Figure 1:
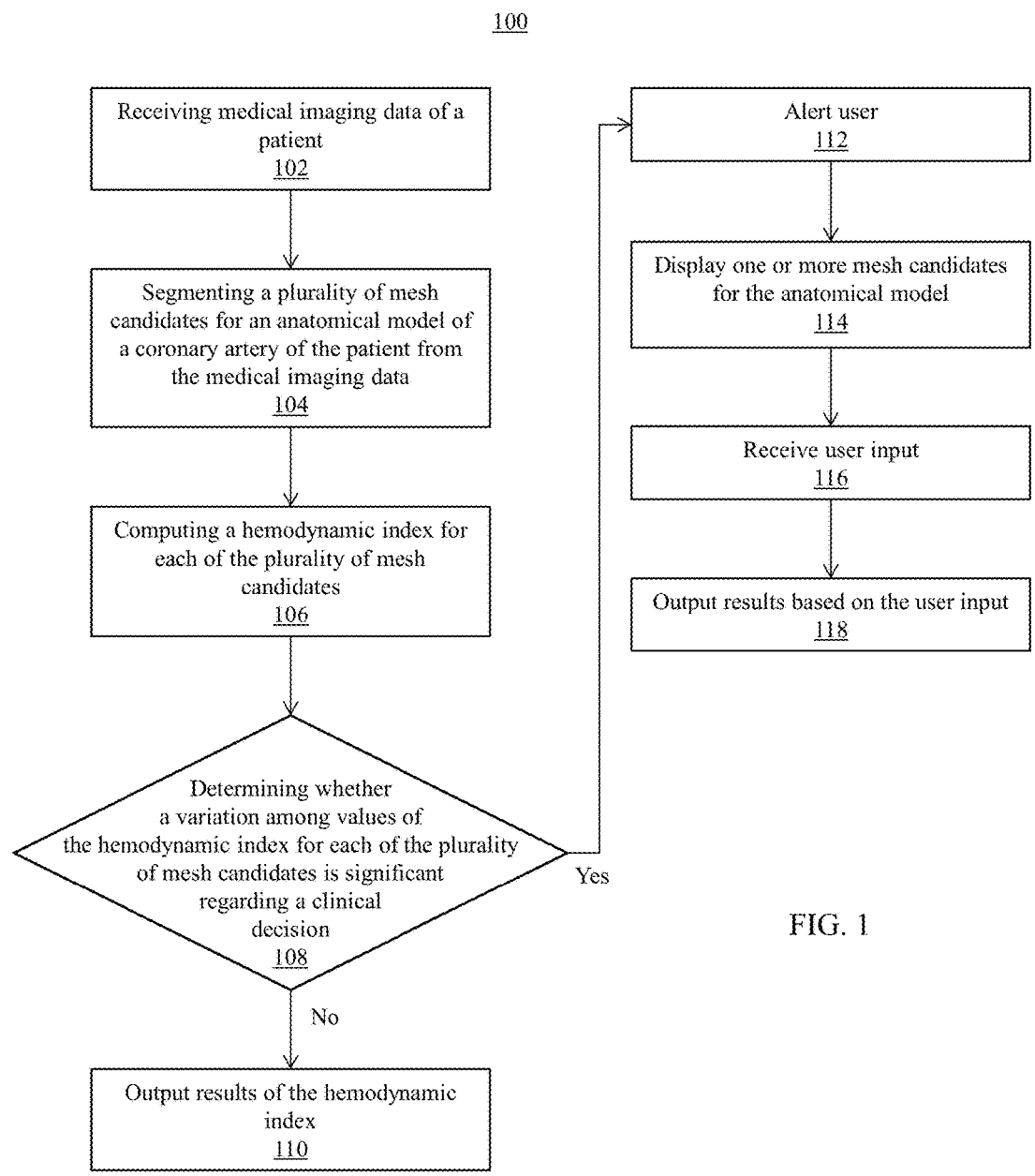
FIG. 1 shows a method for non-invasive assessment of a coronary stenosis, in accordance with one embodiment.

FIG. 1 shows a method 100 for a non-invasive assessment of a coronary stenosis, in accordance with one or more embodiments. Hemodynamic indices are measures relating to the flow of blood. For example, hemodynamic indices may include the FFR and the instantaneous wave-free ratio (iFR). While method 100 of FIG. 1 is described herein with respect to clinical decisions related to a coronary artery stenosis based on hemodynamic indices, it should be understood that the present invention is not so limited, and embodiments of the present invention may be similarly applied for any clinical decision. Method 100 of FIG. 1 provides for improved non-invasive assessment of a coronary stenosis by reducing the amount of user input and interaction.

Referring to FIG. 1, at step 102, medical imaging data of a subject (e.g., a patient) is received. The medical imaging data may include medical images or frames of a target anatomical area of interest of the patient, such as, e.g., the coronary artery of the heart. In one embodiment, the medical imaging data is three dimensional (3D) CT medical imaging data. However, the present invention is not limited thereto, and the medical imaging data may be of any suitable modality, such as, e.g., magnetic resonance imaging (MRI), X-ray angiography, ultrasound (US), etc. In one embodiment, the medical imaging data is received directly from an image acquisition device imaging the patient, such as, e.g., a CT scanner. In another embodiment, the medical imaging data is received by loading previously stored imaging data of the subject from a memory or storage of a computer system.

In an advantageous embodiment, 3D coronary CT angiography (CTA) images are acquired on a CT scanner. The CTA images ensure that the coronary vasculature, including the vessel(s) that contain the stenosis, is adequately imaged using a contrast agent that is injected into the patient. At this stage, the clinician may be provided with an option of identifying lesions (stenoses) of interest by interactively viewing them on the images. This step can also be performed on a patient-specific anatomical model that is extracted from the image data. Alternatively, the stenoses may be automatically detected in the image data using an algorithm for automatic detection of coronary artery stenosis, such as the method for automatic detection of coronary artery stenosis described in United States Published Patent Application No. 2011/0224542, entitled "Method and System for Automatic Detection and Classification of Coronary Stenoses in Cardiac CT Volumes," the disclosure of which is incorporated herein by reference in its entirety. In addition to the medical imaging data, other non-invasive clinical measurements, such as the patient's heart rate and systolic and diastolic blood pressure may also be acquired.

At step 104, a plurality of mesh candidates for an anatomical or geometric surface model of the coronary artery of the patient are segmented from the medical imaging data. In one embodiment, the plurality of mesh candidates may be generated by employing different segmentation methods, such as, e.g., region growing, shape model fitting, graph cuts, machine learning based approaches, or any other suitable segmentation method. Employing a variety of methods will naturally lead to a variety of mesh candidates. Further, in another embodiment, the plurality of mesh candidates may be generated by varying the parameters of a segmentation method. For example, the parameter may be an intensity level used for threshold-based segmentation. A variation in the intensity level will result in a variation of segmentation results.

In a preferred embodiment, the discriminative active shape model framework is employed, where a boundary detector is trained with image features extracted from a local patch. Generally, given an initial estimate of shape (i.e., segmentation), each mesh point is independently adjusted by moving it along the mesh surface normal within a certain range (e.g., [−2, 2 mm]) to an optimal position. Conventionally, a mesh point is moved to a single boundary location identified by the highest score from the boundary detector. Then the mesh is projected into a shape sub-space to enforce prior shape constraints. However, to generate a plurality of segmentation candidates, the discriminative active shape model framework is extended.

Figure 2:
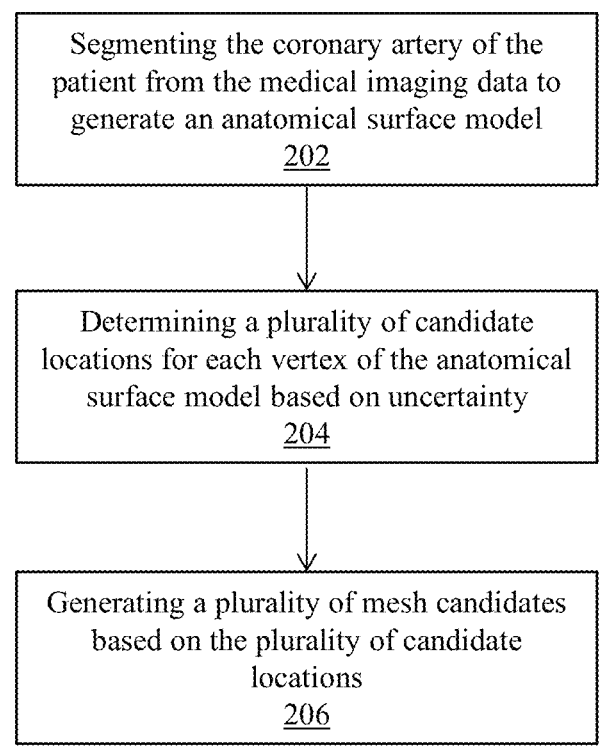
FIG. 2 shows a method for segmenting a plurality of mesh candidates for an anatomical model of a coronary artery of a patient from medical imaging data, in accordance with one embodiment.

Referring for a moment to FIG. 2, a method 104 is shown for segmenting a plurality of mesh candidates for an anatomical model of a coronary artery of the patient from medical imaging data, in accordance with one or more embodiments. Method 104 of FIG. 2 is based on an extended discriminative active shape model framework.

At step 202, the coronary artery of the patient is segmented from the medical imaging data to generate a geometric surface model. In one embodiment, the coronary arteries can be segmented in the medical imaging data using an automated coronary artery centerline extraction algorithm. For example, the coronary arteries can be segmented in a CT volume using the method described United States Published Patent Application No. 2010/0067760, entitled "Method and System for Automatic Coronary Artery Detection," the disclosure of which is incorporated herein by reference in its entirety. Once a coronary artery centerline tree is extracted, cross-section contours can be generated at each point of the centerline tree. The cross-section contour at each centerline point gives a corresponding cross-section area measurement at that point in the coronary artery. Other segmentation methods may also be employed.

An anatomical surface model is then generated for the segmented coronary arteries. For example, methods for anatomical modeling of the coronary arteries are described in U.S. Pat. No. 7,860,290, entitled "Three-Dimensional (3D) Modeling of Coronary Arteries," and U.S. Pat. No. 7,953,266, entitled "Robust Vessel Tree Modeling," the disclosures of which are incorporated herein by reference in their entirety. In addition to the coronaries, the patient-specific anatomical model can include the aortic root together with the proximal part of the aorta. A detailed 3D model of each stenosis can also be extracted using similar algorithms, which includes the quantification of the proximal vessel diameter and area, distal vessel diameter and area, minimal lumen diameter and area, and length of stenosis.

Figure 3:
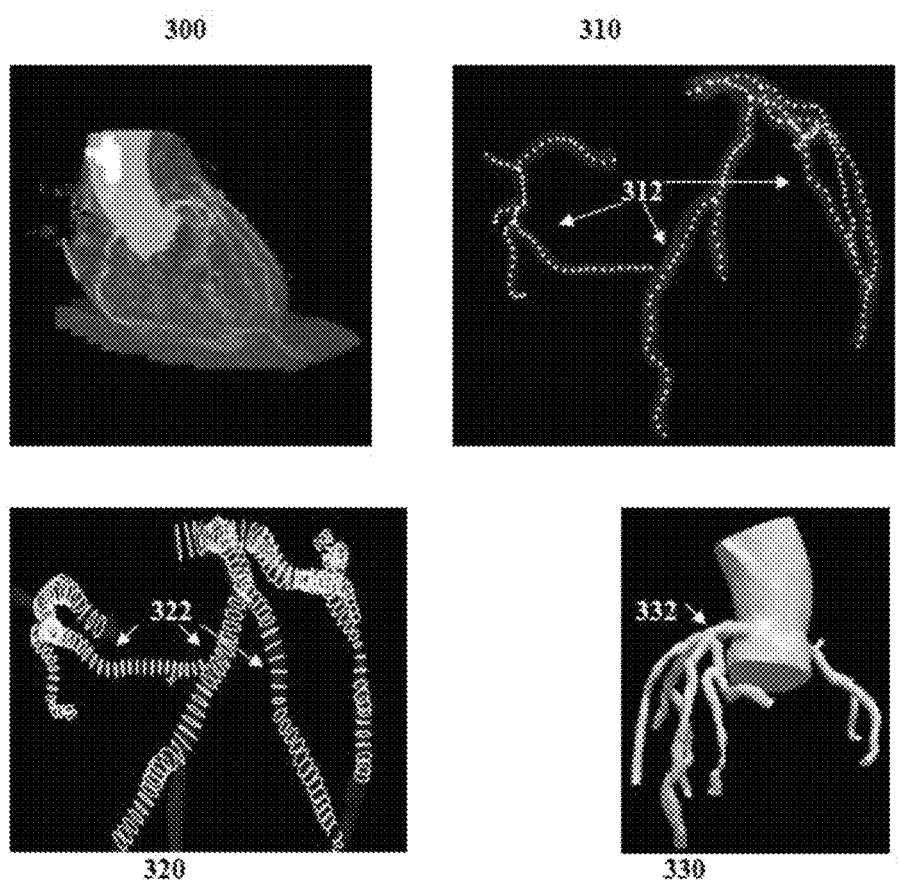
FIG. 3 illustrates exemplary results for generating a patient-specific anatomical model of the coronary vessel tree, in accordance with one embodiment.

FIG. 3 illustrates exemplary results for generating a patient-specific anatomical model of the coronary vessel tree, in accordance with one or more embodiments. Image 300 of FIG. 3 shows coronary CTA data. Image 310 shows a centerline tree 312 extracted from the CTA data. Image 320 shows a cross-section contours 322 extracted at each point of the centerline tree 312. Image 330 shows a 2D surface mesh 332 of the coronary arteries, the aortic root, and the proximal part of the aorta. It is to be understood that the anatomical model of the coronary tree of the patient can be output and displayed, for example on a display screen of the computer system.

Returning to FIG. 2, at step 204, a plurality of candidate locations for each vertex of the anatomical surface model is determined based on uncertainty. Uncertainty or ambiguity in the geometric surface model may be due to, e.g., an image boundary being unclearly delineated or nonexistent, or may be due to the image boundary having multiple responses in a certain range. A range of acceptable boundary points along the surface normal for each vertex is determined. In one embodiment, a classifier, such as, e.g., a probabilistic boosting tree (PBT) classifier, trained with image features extracted from a set of annotated training data, is employed to determine the range of acceptable boundary points for each vertex. Each vertex corresponds to a point on the boundary of the segmented surface. For example, the point may correspond to a pixel or voxel within a range of acceptable boundary points along the surface normal. The trained classifier detects a probability for the points along a surface normal at each point. The range of acceptable boundary points is defined based on the probability values determined by classifier (e.g., as compared to a threshold). The range of acceptable boundary points may correspond to a probability distribution indicating a probability that each point in the range of acceptable boundary points accurately identifies an image boundary.

In one embodiment, for a mesh point with low uncertainty, the mesh point may be moved to the single optimal position associated with the highest probability. For example, a mesh point having a unique peak probability value associated with a location along the surface normal may be considered to have low uncertainty. In another example, a mesh point having a unique probability value satisfying a threshold value may be considered to have low uncertainty. However, if a mesh point has high uncertainty, a plurality of candidate locations for the mesh point is determined based on the uncertainty. In one example, the plurality of candidate locations is determined as each points associated with a peak probability value.

In another embodiment, the probability associated with each mesh point along the surface normal for each vertex of the anatomical surface model is evaluated. Points associated with a probability that satisfies (e.g., exceeds) a threshold value are determined as the plurality of candidate locations.

At step 206, a plurality of mesh candidates is generated based on the plurality of candidate locations. Pursuing all permutations of the plurality of candidate locations would result in too many mesh candidates from a practical standpoint. It would therefore be advantageous to reduce the number of resulting mesh candidates to a manageable number.

In one embodiment, connection rules are enforced to generate the plurality of mesh candidates from the plurality of candidate locations. One example of a connection rule includes a rule to connect the outer layer candidate locations associated with each neighboring vertex (i.e., mesh point). Other examples of connection rules include a rule to connect the inner layer or the median layer of the candidate locations associated with each neighboring vertex, or a rule to connect average locations of the candidate locations of each vertex. Other connection rules resulting in additional mesh candidates can be used as well.

Each of the plurality of mesh candidates is projected onto a learned shape sub-space of the coronary artery using an active shape model. In addition to enforcing prior shape constraints for each mesh candidate, projecting a mesh candidate onto the shape sub-space has the effect of smoothing out the mesh candidate and removing outlier candidate locations on the individual surface normals.

In a further embodiment, a confidence score may be assigned to each mesh candidate. For example, the confidence score may be the average probability score of the respective candidate locations determined by the boundary detector. Cluster analysis may then be applied to reduce the plurality of mesh candidates by preserving distinct segmentations with highest scores.

Returning to FIG. 1, at step 106, a hemodynamic index for a stenosis is computed for each of the plurality of mesh candidates. In one embodiment, the hemodynamic index for the stenosis includes the FFR. The FFR of a stenosis is a representation of the pressure drop across the stenosis for a patient at hyperemia. The FFR for a stenosis may be represented as in equation (1).

$$FFR=P_d/P_a(\text{hyperemia}) \tag{1}$$

The pressure drop over the stenosis during hyperemia may be determined using a computational fluid dynamics (CFD) algorithm that simulates a hyperemia by employing appropriate boundary conditions in the CFD algorithm and using the results of the CFD algorithm to determine the pressure drop at hyperemia. For example, such simulations may be performed using the method described in U.S. patent application Ser. No. 13/794,113, entitled "Method and System for Non-Invasive Functional Assessment of Coronary Artery Stenosis," and U.S. patent application Ser. No. 14/070,810, entitled "Method and System for Non-Invasive Functional Assessment of Coronary Artery Stenosis," the disclosures of which are incorporated herein by reference in their entirety. In other embodiments, the FFR may be determined by a machine learning-based algorithm, where features extracted from the medical imaging data (or from a geometric model constructed from the medical imaging data) are used with a trained classifier to compute the FFR value. Such machine learning-based algorithms may be performed using the method described in U.S. patent application Ser. No. 14/516,163, entitled "Method and System for Machine Learning Based Assessment of Fractional Flow Reserve," the disclosure of which is incorporated herein by reference in its entirety.

In another embodiment, the hemodynamic index includes the iFR. The iFR provides an indication as to whether a stenosis is causing a limitation of blood flow in the coronary arteries. For example, the iFR may be non-invasively computed based on blood flow and pressure simulations using the method described in U.S. patent application Ser. No. 14/689,083, entitled "Method and System for Non-Invasive Computation of Hemodynamic Indices for Coronary Artery Stenosis," the disclosure of which is incorporated herein by reference in its entirety. Other hemodynamic indices may also be used.

At step 108, a determination is made whether a variation among values of the hemodynamic index of a stenosis for each of the plurality of mesh candidates is significant regarding a clinical decision. For example, a variation among the FFR values that is limited to entirely above or entirely below a threshold value (e.g., 0.8) is unambiguous and is not significant regarding the clinical decision of treatment of a stenosis. There is no need for the user to choose one of the candidate solutions over the others.

Figure 4:
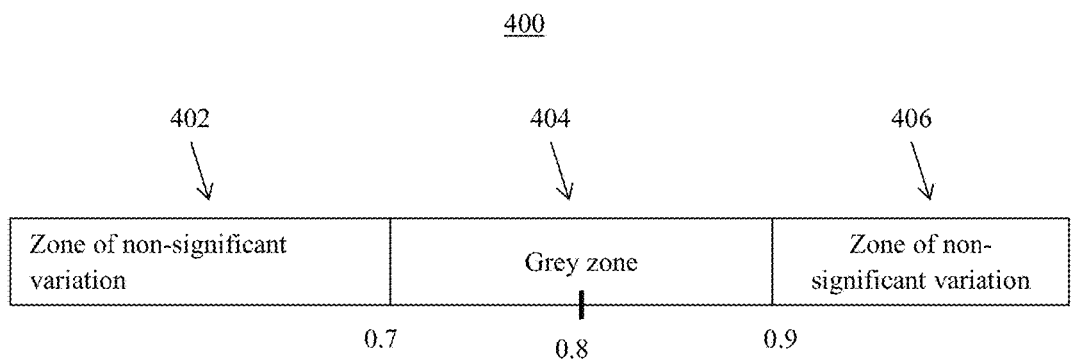
FIG. 4 shows a range of FFR values having a grey zone, in accordance with one embodiment.

While the embodiments herein may be discussed with respect to a single threshold value resulting in a binary decision (e.g., decision to treat a stenosis or not treat a stenosis based on threshold FFR value of 0.8), it should be understood that in some embodiments, any number of threshold values may be employed resulting in a plurality of ranges of values corresponding to a plurality of categories. For example, in one embodiment, the range of values resulting from a hemodynamic index may include a grey zone of values where there is no clear clinical decision support. FIG. 4 shows a range of FFR values 400, in accordance with one or more embodiments. Range of values 400 includes zones 402, 404, and 406. Zone 402 is referred to as a black zone with FFR values below a first threshold value of 0.7. Zone 406 is referred to as a white zone with FFR values above a second threshold value of 0.9. Black zone 402 and white zone 406 correspond to FFR values that have non-significant variation with respect to the clinical decision of whether to treat a stenosis. Zone 404 between the first threshold value and the second threshold value is referred to as the grey zone where there is no clear decision on whether to treat the stenosis. Other threshold values of the first and second threshold values may also be used to define the zones. For example, the threshold values may be inferred from clinical data (e.g., by observing the performance of cFFR against the invasive FFR results) or may be set by the user.

If it is determined that the variation is not significant, method 100 proceeds to step 110. If it is determined that the variation is significant, method 100 proceeds to step 112.

At step 110, if the variation is not significant regarding a clinical decision, results of the hemodynamic index computation for the plurality of mesh candidates are output, e.g., using a display device. For example, the output of the results of the FFR value may include displaying a range of the FFR values for the stenosis for the plurality of mesh candidates. In another example, the output of the results of the FFR value may include displaying a list of FFR values for the stenosis for each of the plurality of mesh candidates. In some embodiments, for extra quality control, a user may choose to interactively access visualizations of the segmentation results using, e.g., an input/output device. In other embodiments, the visualizations of the segmentation results (mesh candidates) are provided by default.

At step 112, if the variation is significant regarding a clinical decision, a user is alerted that user input and interaction is advised. For example, the user may be advised to further analyze segmentation results.

At step 114, one or more of the mesh candidates for the anatomical model are displayed. In an advantageous embodiment for displaying mesh candidates to enable user selection, multiplanar reformatted (MPR) planes are generated from the medical imaging data. The MPR planes depict vessel cross-sections (essentially perpendicular to the vessel centerline) and vessel segments (aligned with the vessel centerline). In one embodiment, the MPR plane locations may also be displayed in the original medical imaging data or in a model or other representation of the anatomical object. In some embodiments, the MPR planes may be generated based on where the relevant features in the anatomical object (e.g., stenosis in a coronary tree) are located and/or where the relevant discrepancies between mesh candidates occur. The stenosis locations may be detected automatically by measuring the vessel diameter along the vessel centerlines. In other embodiments, the user may select MPR plane locations.

The mesh candidates may be overlaid on the MPR planes as thin and/or semi-transparent lines to enable a user to compare how each mesh candidate fits to the original medical imaging data. In some embodiments, a plurality of mesh candidates may be displayed simultaneously on a same MPR plane, with different mesh candidates being represented with different colors, different patterns (e.g., solid lines, dash lines, etc.), or any other visual differentiator. In other embodiments, mesh candidates may be displayed in a side-by-side configuration, where each displayed mesh candidate is overlaid on a separate instance of a same MPR plane. Mesh candidates may also be displayed in 3D.

Figure 5:
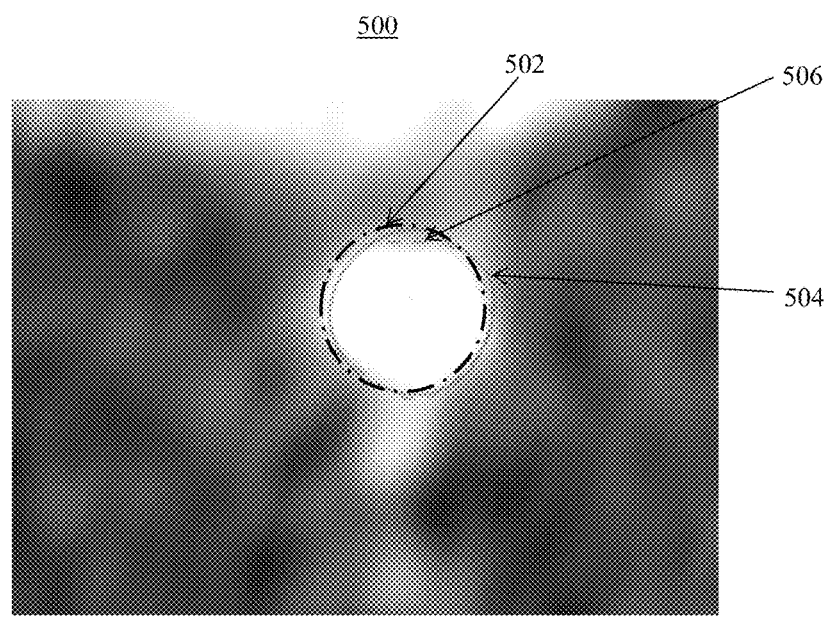
FIG. 5 depicts MPR planes having a plurality of mesh candidates overlaid thereon, in accordance with one embodiment.

FIG. 5 depicts MPR planes 500 having a plurality of mesh candidates overlaid thereon, in accordance with one or more embodiments. MPR planes 500 include mesh candidates 502 (represented as dash dotted lines), 504 (represented as a solid line), and 506 (represented as dashed lines). Mesh candidates 502, 504, and 506 may also be represented using different colors to represent different candidates. Other visual differentiators are also contemplated.

In one advantageous embodiment, all mesh candidates for which the hemodynamic index of the stenosis is above a threshold value may be displayed on a first portion of a display over a set of MPR planes and all mesh candidates for which the hemodynamic index of the stenosis is below a threshold value may be displayed on a second portion of the display of instances of the same set of MPR planes. For example, the threshold value may be based on the clinical decision. In the example of the FFR, the threshold value may be 0.8. In some embodiments, to aid the user in making a fast assessment, the location where segmentations diverge the most may be indicate, e.g., with overlaid arrows pointing to these locations or other visual differentiators.

In some embodiments, probabilities of each mesh candidate are displayed. Each probability indicates the confidence in the accuracy of the initial measurements extracted from the image. For example, the probabilities may be calculated as part of the segmentation method and may be expressed as relative number to aid in comparing the different candidate solutions.

Returning to FIG. 1, at step 116, user input is received. In one embodiment, user input may be received to select a mesh candidate that is the most accurate. For example, the mesh candidate with the highest probability may be displayed for the user and, upon review, the user may select that mesh candidate having the highest probability for the anatomical model. In another example, the mesh candidates having the top N probabilities are displayed for the user and, upon review, the user may select one of the mesh candidates having the top N probabilities for the anatomical model. In a further example, if a threshold number or proportion of mesh candidates is not significant regarding a clinical decision, the remaining mesh candidates are displayed for the user to review as possible outliers. An example of this is where nearly all mesh candidates result in an FFR value that is above (or below in other examples) a threshold FFR value of 0.8, and a few remaining mesh candidates result in an FFR value that is below (or above in other example) the threshold FFR value of 0.8, the few remaining mesh candidates may be displayed for the user and, upon review, the user may dismiss those few remaining mesh candidates as outliers.

In another embodiment, such as where the user is not satisfied with any of the segmentation results, user input may be received to edit one or more of the segmentation results using the medical imaging data of the patient until the user is satisfied. Editing segmentation results may be performed in response to user input received via input/output devices, such as, e.g., a mouse, a touchscreen, etc., using known methods.

At step 118, results are output based on the user input, e.g., using a display device. The results may include hemodynamic index values (e.g., FFR values), the selected mesh candidate, or any other pertinent information.

While the embodiments described herein are generally discussed with respect to clinical decisions based on hemodynamic indices, such as, e.g., the FFR, it should understood that the present invention is not so limited. The FFR is only one example application of the embodiments discussed herein. Embodiments of the present invention may be similarly applied for any clinical decision or any non-clinical decision. Embodiments of the present invention may be applied where a final value is calculated from measurements extracted from initial data, and where an inaccuracy in these measurements becomes relevant only if it tips the final value beyond a critical threshold value. If multiple candidate solutions all agree on whether or not a critical value is reached, a user does not need to interfere and make corrections or selections.

Other exemplary applications of the embodiments of the present invention include aortic valve stenosis, standard quantitative coronary angiography (QCA) for lesion grading, and sizing of grafts, stents, valves, etc. Other applications are also contemplated. For the aortic valve stenosis, the aortic valve orifice area is used for classifying the stenosis as mild, moderate, or severe based on some predefined cutoff value. It is not necessary to select or edit mesh segmentation candidates as long as the classification is preserved. Standard QCA may be used for lesion grading (e.g., less than 50%, 50-70%, 70-90%, or greater than 90%). As long as all segmentation candidates point to a same lesion grading category, there is no need for further refinement or editing of the segmentation. Segmentation is often used to assess the size of the anatomical structure for sizing of grafts, stents, valves, etc. Devices typically come in standard fixed sizes. As long as all segmentation candidates point to one standard device size, there is no need to further refine the segmentation.

Figure 6:
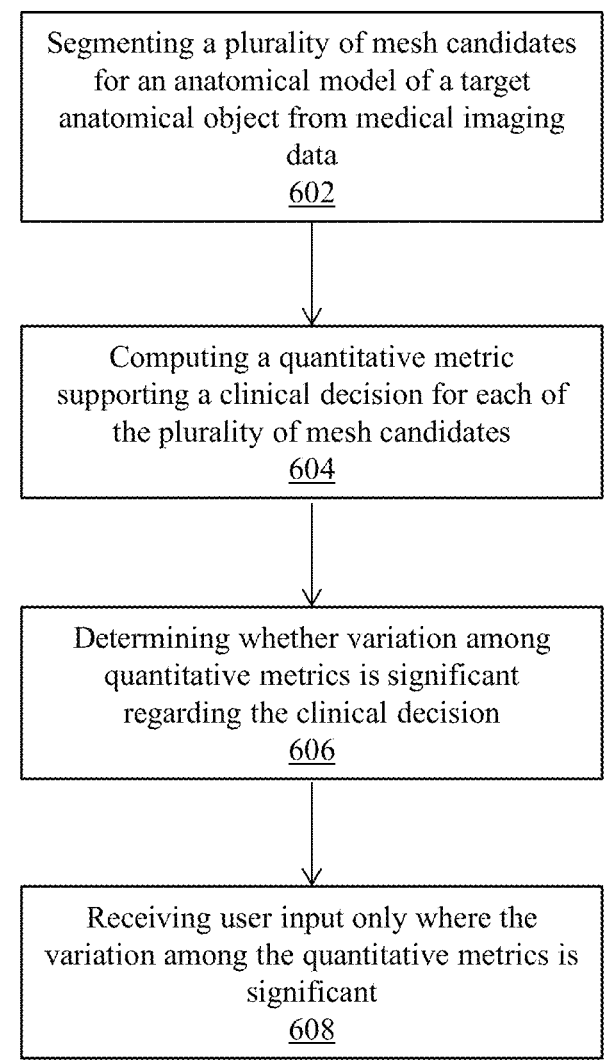
FIG. 6 shows a method for improving the workflow of a clinical decision, in accordance with one embodiment.

For example, FIG. 6 shows a method 600 for improving the workflow of a clinical decision, in accordance with one or more embodiments. Method 600 may be applied for any clinical decision. At step 602, a plurality of mesh candidates for an anatomical model of a target anatomical object are segmented from medical imaging data. At step 604, a quantitative metric is computed supporting a clinical decision for each of the plurality of mesh candidates. The quantitative metric may include any quantitative metric, such as, e.g., a diameter of a stenosis, a length of a stenosis, etc. In some embodiments, the quantitative metric is not determined from the segmentation. At step 606, it is determined whether variation among quantitative metrics is significant regarding the clinical decision. In particular, the quantitative metric computed for each of the plurality of mesh candidates is compared to a threshold. Variation among quantitative metrics is determined to not be significant regarding the clinical decision where, for example, the quantitative metrics for each of the plurality of mesh candidates are all above or all below the threshold. Variation among quantitative metrics is determined to be significant regarding the clinical decision where, for example, the quantitative metrics for each of the plurality of mesh candidates span the threshold such that some of the quantitative metrics are above the threshold and some of the quantitative metrics are below the threshold. At step 608, user input is only received for the determining the clinical decision where the variation among quantitative metrics is determined to be significant.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIGS. 1-2 and 6. Certain steps of the methods described herein, including one or more of the steps of FIGS. 1-2 and 6, may be performed by a server or by another processor in a network-based cloud-computing system. Certain steps of the methods described herein, including one or more of the steps of FIGS. 1-2 and 6, may be performed by a client computer in a network-based cloud computing system. The steps of the methods described herein, including one or more of the steps of FIGS. 1-2 and 6, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 1-2 and 6, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 7:
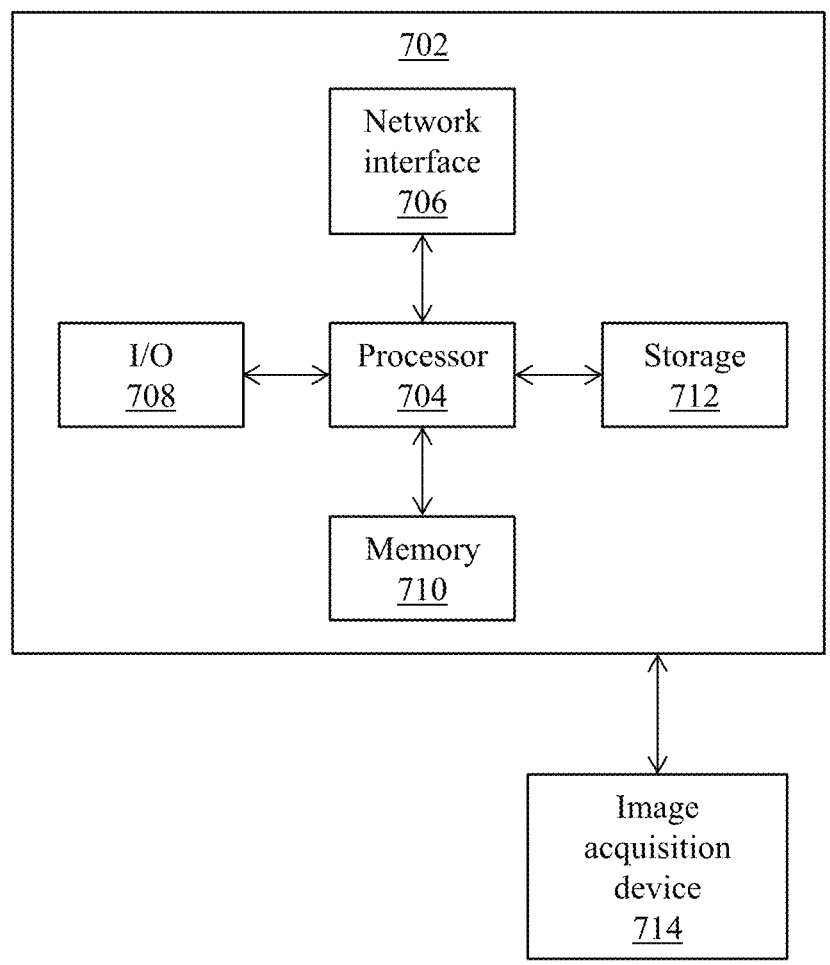
FIG. 7 shows a high-level block diagram of a computer for improving the workflow of a clinical decision based on hemodynamic indices, in accordance with one embodiment.

A high-level block diagram 700 of an example computer that may be used to implement systems, apparatus, and methods described herein is depicted in FIG. 7. Computer 702 includes a processor 704 operatively coupled to a data storage device 712 and a memory 710. Processor 704 controls the overall operation of computer 702 by executing computer program instructions that define such operations. The computer program instructions may be stored in data storage device 712, or other computer readable medium, and loaded into memory 710 when execution of the computer program instructions is desired. Thus, the method steps of FIGS. 1-2 and 6 can be defined by the computer program instructions stored in memory 710 and/or data storage device 712 and controlled by processor 704 executing the computer program instructions. For example, the computer program instructions can be implemented as computer executable code programmed by one skilled in the art to perform the method steps of FIGS. 1-2 and 6. Accordingly, by executing the computer program instructions, the processor 704 executes the method steps of FIGS. 1-2 and 6. An image acquisition device 714, such as a CT scanning device, C-arm image acquisition device, MR scanning device, Ultrasound device, etc., can be connected to the computer 702 to input image data to the computer 702. It is possible to implement the image acquisition device 714 and the computer 702 as one device. It is also possible that the image acquisition device 712 and the computer 702 communicate wirelessly through a network. Computer 704 may also include one or more network interfaces 706 for communicating with other devices via a network. Computer 702 may also include one or more input/output devices 708 that enable user interaction with computer 702 (e.g., display, keyboard, mouse, speakers, buttons, etc.).

Processor 704 may include both general and special purpose microprocessors, and may be the sole processor or one of multiple processors of computer 702. Processor 704 may include one or more central processing units (CPUs), for example. Processor 704, data storage device 712, and/or memory 710 may include, be supplemented by, or incorporated in, one or more application-specific integrated circuits (ASICs) and/or one or more field programmable gate arrays (FPGAs).

Data storage device 712 and memory 710 each include a tangible non-transitory computer readable storage medium. Data storage device 712, and memory 710, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 708 may include peripherals, such as a printer, scanner, display screen, etc. For example, input/output devices 780 may include a display device such as a cathode ray tube (CRT) or liquid crystal display (LCD) monitor for displaying information to the user, a keyboard, and a pointing device such as a mouse or a trackball by which the user can provide input to computer 702.

Any or all of the systems and apparatus discussed herein, may be implemented using one or more computers such as computer 702.

One skilled in the art will recognize that an implementation of an actual computer or computer system may have other structures and may contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for non-invasive assessment of an arterial stenosis, comprising:
    segmenting a plurality of mesh candidates for an anatomical model of an artery including a stenosis region of a patient from medical imaging data, the plurality of mesh candidates representing different anatomical models of the artery resulting from variations in segmenting techniques, wherein segmenting the plurality of mesh candidates comprises:
        determining one or more candidate locations for each vertex of the anatomical model,
        assigning a confidence score to each of the plurality of mesh candidates by averaging a probability associated with each vertex in a respective mesh candidate, and
        applying cluster analysis to reduce a number of the plurality of mesh candidates based on the confidence score;
    computing a hemodynamic index for the stenosis region in each of the plurality of mesh candidates; and
    determining whether a clinical decision for treatment of the stenosis region of the patient is ambiguous by determining whether a variation among values of the hemodynamic index for the stenosis region in each of the plurality of mesh candidates is entirely below a threshold for the clinical decision or is entirely above the threshold for the clinical decision.

2. The method as recited in claim 1, wherein segmenting a plurality of mesh candidates for an anatomical model of an artery including a stenosis region of a patient from medical imaging data comprises:
    generating the plurality of mesh candidates based on the one or more candidate locations.

3. The method as recited in claim 1, wherein determining one or more candidate locations for each vertex of the anatomical model comprises:
    determining the probability that a respective voxel is a boundary point for each voxel along a surface normal within a predetermined distance at each vertex.

4. The method as recited in claim 3, wherein determining one or more candidate locations for each vertex of the anatomical model further comprises:
    determining voxels associated with a probability above a threshold value as the one or more candidate locations for each vertex.

5. The method as recited in claim 2, wherein generating the plurality of mesh candidates based on the one or more candidate locations comprises:
generating the plurality of mesh candidates by enforcing a plurality of connection rules for connecting the one or more candidate locations of neighboring vertices of the anatomical model, wherein each of the plurality of connection rules results in a corresponding mesh candidate.

6. The method as recited in claim 5, wherein generating the plurality of mesh candidates based on the one or more candidate locations further comprises:
projecting each of the plurality of mesh candidates onto a learned shape space of the artery using an active shape model.

7. The method as recited in claim 1, further comprising:
in response to determining that the clinical decision for treatment of the stenosis region of the patient is not ambiguous, displaying results of the hemodynamic index without receiving user input.

8. The method as recited in claim 1, further comprising:
in response to determining that the clinical decision for treatment of the stenosis region of the patient is ambiguous:
displaying at least one of the plurality of mesh candidates; and
receiving user input to select and/or edit the at least one of the plurality of mesh candidates.

9. The method as recited in claim 8, wherein displaying at least one of the plurality of mesh candidates comprises:
displaying each of the plurality of mesh candidates overlaid on a same multiplanar reformatted planes of the artery.

10. The method as recited in claim 8, wherein displaying at least one of the plurality of mesh candidates comprises:
displaying each of the plurality of mesh candidates overlaid on an instance of a same multiplanar reformatted planes of the artery in a side-by-side configuration.

11. The method as recited in claim 8, wherein displaying at least one of the plurality of mesh candidates comprises:
displaying mesh candidates of the plurality of mesh candidates having a value of the hemodynamic index for the stenosis region above the threshold on a first portion of a display; and
displaying mesh candidates of the plurality of mesh candidates having the value of the hemodynamic index for the stenosis region below the threshold on a second portion of the display.

12. The method as recited in claim 1, wherein computing a hemodynamic index for the stenosis region in each of the plurality of mesh candidates comprises:
simulating blood flow and pressure in each of the plurality of mesh candidates for the artery of the patient; and
computing a fractional flow reserve value for the stenosis region in each of the plurality of mesh candidates based on the blood flow and pressure simulations.

13. An apparatus for non-invasive assessment of an arterial stenosis, comprising:
means for segmenting a plurality of mesh candidates for an anatomical model of an artery including a stenosis region of a patient from medical imaging data, the plurality of mesh candidates representing different anatomical models of the artery resulting from variations in segmenting techniques, wherein the means for segmenting the plurality of mesh candidates comprises:
means for determining one or more candidate locations for each vertex of the anatomical model,
means for assigning a confidence score to each of the plurality of mesh candidates by averaging a probability associated with each vertex in a respective mesh candidate, and
means for applying cluster analysis to reduce a number of the plurality of mesh candidates based on the confidence score;
means for computing a hemodynamic index for the stenosis region in each of the plurality of mesh candidates; and
means for determining whether a clinical decision for treatment of the stenosis region of the patient is ambiguous by determining whether a variation among values of the hemodynamic index for the stenosis region in each of the plurality of mesh candidates is entirely below a threshold for the clinical decision or is entirely above the threshold for the clinical decision.

14. The apparatus as recited in claim 13, wherein the means for segmenting a plurality of mesh candidates for an anatomical model of an artery including a stenosis region of a patient from medical imaging data comprises:
means for generating the plurality of mesh candidates based on the one or more candidate locations.

15. The apparatus as recited in claim 13, wherein the means for determining one or more candidate locations for each vertex of the anatomical model comprises:
means for determining the probability that a respective voxel is a boundary point for each voxel along a surface normal within a predetermined distance at each vertex.

16. The apparatus as recited in claim 15, wherein the means for determining one or more candidate locations for each vertex of the anatomical model further comprises:
means for determining voxels associated with a probability above a threshold value as the one or more candidate locations for each vertex.

17. The apparatus as recited in claim 14, wherein the means for generating the plurality of mesh candidates based on the one or more candidate locations comprises:
means for generating the plurality of mesh candidates by enforcing a plurality of connection rules for connecting the one or more candidate locations of neighboring vertices of the anatomical model, wherein each of the plurality of connection rules results in a corresponding mesh candidate.

18. The apparatus as recited in claim 17, wherein the means for generating the plurality of mesh candidates based on the one or more candidate locations further comprises:
means for projecting each of the plurality of mesh candidates onto a learned shape space of the artery using an active shape model.

19. The apparatus as recited in claim 13, further comprising:
means, responsive to determining that the clinical decision for treatment of the stenosis region of the patient is not ambiguous, for displaying results of the hemodynamic index without receiving user input.

20. The apparatus as recited in claim 13, further comprising:
means, responsive to determining that the clinical decision for treatment of the stenosis region of the patient is ambiguous, for:
displaying at least one of the plurality of mesh candidates; and
receiving user input to select and/or edit the at feast one of the plurality of mesh candidates.

21. A non-transitory computer readable medium storing computer program instructions for non-invasive assessment of an arterial stenosis, the computer program instructions when executed by a processor cause the processor to perform operations comprising:

segmenting a plurality of mesh candidates for an anatomical model of an artery including a stenosis region of a patient from medical imaging data, the plurality of mesh candidates representing different anatomical models of the artery resulting from variations in segmenting techniques, wherein segmenting the plurality of mesh candidates comprises:

determining one or more candidate locations for each vertex of the anatomical model, assigning a confidence score to each of the plurality of mesh candidates by averaging a probability associated with each vertex in a respective mesh candidate, and applying cluster analysis to reduce a number of the plurality of mesh candidates based on the confidence score;

computing a hemodynamic index for the stenosis region in each of the plurality of mesh candidates; and determining whether a clinical decision for treatment of the stenosis region of the patient is ambiguous by determining whether a variation among values of the hemodynamic index for the stenosis region in each of the plurality of mesh candidates is entirely below a threshold for the clinical decision or is entirely above the threshold for the clinical decision.

22. The non-transitory computer readable medium as recited in claim 21, wherein segmenting a plurality of mesh candidates for an anatomical model of an artery including a stenosis region of a patient from medical imaging data comprises:

generating the plurality of mesh candidates based on the one or more candidate locations.

23. The non-transitory computer readable medium as recited in claim 21, the operations further comprising:

in response to determining that the clinical decision for treatment of the stenosis region of the patient is not ambiguous, displaying results of the hemodynamic index without receiving user input.

24. The non-transitory computer readable medium as recited in claim 21, the operations further comprising:

in response to determining that the clinical decision for treatment of the stenosis region of the patient is ambiguous:

displaying at least one of the plurality of mesh candidates; and receiving user input to select and/or edit the at least one of the plurality of mesh candidates.

25. The non-transitory computer readable medium as recited in claim 24, wherein displaying at least one of the plurality of mesh candidates comprises:

displaying each of the plurality of mesh candidates overlaid on a same multiplanar reformatted planes of the artery.

26. A method for supporting a clinical decision regarding an anatomical object of interest, comprising:

segmenting a plurality of mesh candidates for an anatomical model of an anatomical object of interest of a patient from medical imaging data, the plurality of mesh candidates representing different anatomical models of the artery resulting from variations in segmenting techniques, wherein segmenting the plurality of mesh candidates comprises:

determining one or more candidate locations for each vertex of the anatomical model, assigning a confidence score to each of the plurality of mesh candidates by averaging a probability associated with each vertex in a respective mesh candidate, and applying cluster analysis to reduce a number of the plurality of mesh candidates based on the confidence score;

computing a quantitative metric for each of the plurality of mesh candidates; and determining whether a clinical decision is ambiguous by determining whether a variation among values of the quantitative metric for each of the plurality of mesh candidates is entirely below a threshold for the clinical decision or is entirely above the threshold for the clinical decision.

\* \* \* \* \*